United States Patent [19]

Nakae et al.

[11] Patent Number: 5,298,147
[45] Date of Patent: Mar. 29, 1994

[54] OXYGEN CONCENTRATION SENSOR

[75] Inventors: Makoto Nakae; Masahiro Shibata, both of Nagoya; Yoshiki Chujo, Mishima, all of Japan

[73] Assignees: Nippondenso Co., Ltd., Kariya; Toyota Jidosha Kabushiki Kaisha, Toyota, both of Japan

[21] Appl. No.: 888,107

[22] Filed: May 26, 1992

[30] Foreign Application Priority Data

May 27, 1991 [JP] Japan .................................. 3-121278
May 8, 1992 [JP] Japan .................................. 4-116292

[51] Int. Cl.$^5$ .............................................. G01N 27/26
[52] U.S. Cl. .................................. 204/424; 204/425; 204/426; 204/427; 204/428
[58] Field of Search ............... 204/424, 425, 426, 427, 204/428

[56] References Cited

U.S. PATENT DOCUMENTS

| | | | |
|---|---|---|---|
| 4,158,166 | 6/1979 | Isenberg | 204/421 |
| 4,272,329 | 6/1981 | Hetrick et al. | 204/425 |
| 4,772,376 | 9/1988 | Yukawa et al. | 204/425 |
| 4,938,861 | 7/1990 | Kurosawa et al. | 204/425 |

FOREIGN PATENT DOCUMENTS

| | | |
|---|---|---|
| 56-130649 | 10/1981 | Japan . |
| 58-153155 | 9/1983 | Japan . |
| 60-39548 | 3/1985 | Japan . |
| 60-138263 | 7/1985 | Japan . |
| 60-55777 | 12/1985 | Japan . |
| 61-247839 | 11/1986 | Japan . |

Primary Examiner—John Niebling
Assistant Examiner—Bruce F. Bell
Attorney, Agent, or Firm—Cushman, Darby & Cushman

[57] ABSTRACT

An oxygen concentration sensor of this invention comprises an element and a diffusion hole. The element is exposed to a gas to be measured and has a chamber portion formed together with an oxygen ion conductive solid electrolyte. The diffusion hole is provided for restricting the flow of said gas to be measured into said chamber portion. Furthermore, the relationship $1 \leq S/(L \cdot V) \leq 5$ is established with the diffusion hole having a cross sectional area S (mm$^2$) and a length L (mm) and the chamber portion having a volume V (mm$^3$). To do so, the oxygen concentration sensor can provide a stable output even if a pressure of the gas to be measured is abruptly changed.

3 Claims, 9 Drawing Sheets

OXYGEN CONCENTRATION SENSOR

BACKGROUND OF THE INVENTION

Field of the Invention

The present invention relates to an oxygen concentration sensor capable of stably sensing an oxygen concentration even if a pressure of a gas to be measured is abruptly varied.

Description of the Related Art

As disclosed, for example, in Japanese Patent Unexamined Publication No. 56-130649, a conventional oxygen concentration sensor is arranged such that a chamber portion is composed of a tube having opposite open ends and a pin-hole-shaped diffusion hole partially defined to the tube and solid electrolytes closing the opposite open ends, pump electrodes being formed on the opposite confronting surfaces of one of the solid electrolytes and sensor electrodes being formed on the opposite confronting surfaces of the other of the solid electrolytes.

With the above arrangement, an oxygen partial pressure difference is produced between a pressure inside the chamber portion and a pressure of a gas to be measured in the outside of the chamber portion through the diffusion hole and an oxygen concentration electromotive force produced by this oxygen partial pressure difference is sensed by the sensor electrodes. A voltage imposed on the pump electrodes is controlled so that the oxygen concentration electromotive force has a constant value even if the oxygen partial pressure difference between the pressure outside the chamber portion and the gas to be measured inside the chamber portion is changed as the oxygen concentration in the gas to be measured changes and thus the oxygen concentration of the gas to be measured is sensed by an imposed amount of the voltage. Further, oxygen concentration sensors operating in the same way as the above are also disclosed in Japanese Patent Unexamined Publication Nos. 58-153155 and 60-39548.

FIGS. 14 and 15 show the state of a sensor output corresponding to a change of a pressure outside an oxygen concentration sensor arranged as described above.

As shown in FIG. 14, since the oxygen concentration sensor having the conventional arrangement as described above has no pressure dependency on a static pressure change as a gradual pressure change arisen, for example, in the exhaust pipe of an internal combustion engine, this oxygen concentration sensor is effective for correctly sensing an oxygen concentration under the operating conditions where a large static pressure variation is produced.

As shown in FIG. 15, however, when the oxygen concentration sensor having the pin hole serving as the diffusion hole is located at a position such as the suction pipe of an internal combustion engine and the like where a dynamic pressure change as an abrupt pressure change is arisen, a problem arises in that an output from the oxygen concentration sensor is greatly changed and thus an oxygen concentration cannot be correctly sensed.

Consequently, as shown in FIG. 16 for example, since the conventional oxygen concentration sensor is subjected to an abrupt pressure change due to a change of an engine r.p.m, the sensor cannot provide a stable output from a sensor which is not affected by the engine r.p.m, and as a result cannot correctly sense an oxygen concentration, and thus the conventional oxygen concentration sensor cannot be disposed at the suction pipe of the internal combustion engine for sensing an oxygen concentration.

Nevertheless, the need for regulating an exhaust gas is further increased as well as an improvement of a fuel cost of an internal combustion engine is required at present and thus the need for controlling a mixed amount of an intake air and EGR gas by using an oxygen concentration sensor to thereby adjust the mixed amount to an optimum EGR ratio is increased, by which the oxygen concentration sensor is required to be mounted on the suction pipe.

SUMMARY OF THE INVENTION

An object of the present invention is to provide an oxygen concentration sensor capable of correctly sensing an oxygen concentration when it is mounted not only at a location where a static pressure variation occurs but also at a location such as the suction pipe of an internal combustion engine where a dynamic pressure variation occurs.

According to the present invention, as a result of the examination of the cause of the above problem, it has been found that the reason why a sensor output is changed by a dynamic pressure variation in a conventional oxygen concentration sensor is as described below.

In the conventional oxygen concentration sensor, an amount of a gas to be measured flowing into a chamber through a diffusion hole is balanced with an amount of oxygen ions transmitted by pump electrodes from the inside of a chamber portion to the outside thereof. When a pressure of the gas to be measured is abruptly increased, however, an amount of the gas to be measured flowing into the chamber portion through the diffusion hole is made larger than a required amount by a pressure difference between the gas to be measured and a pressure inside the chamber portion, and thus an oxygen partial pressure in the chamber portion is made higher than an oxygen partial pressure of the gas to be actually measured. Consequently, a sensor outputs an oxygen concentration value higher than that of an oxygen concentration of the actually measured gas until the oxygen partial pressure in the chamber portion is balanced with that of the measured gas.

Thus, the inventors have found that, when a diffusion hole communicating a gas to be measured in the outside of a chamber portion with the inside of the chamber portion has a specific cross sectional area and length and when a chamber portion has a specific volume, there can be removed the prior art defect by providing an oxygen concentration sensor in which a pressure in the chamber portion can sufficiently follow to a dynamic pressure variation of a gas to be measured, and according to the present invention, there is provided a oxygen concentration sensor having the relationship $1 \leq S(L \cdot V) \leq 5$ is established, where a diffusion hole has a cross sectional area S (mm$^2$) and length L (mm) and a chamber portion has a volume V (mm$^3$).

With the oxygen concentration sensor according to the present invention, a pressure in the chamber portion can be changed following to a pressure of a gas to be measured even if a pressure of the gas to be measured is abruptly changed, by adopting such arrangements that a cross sectional area of the diffusion hole of the oxygen concentration sensor is increased, that a length of the diffusion hole is shortened and that a volume of the chamber portion is reduced. As a result, since a pressure difference between a pressure outside the chamber portion and a pressure inside the chamber portion is difficult to be arisen, an amount of the gas to be measured flowing into the chamber portion thorough the diffusion hole can be maintained constant without being affected by a dynamic pressure variation of the gas to be measured, and thus a sensor output can be stably maintained and the oxygen concentration sensor which is not affected by abrupt dynamic pressure change of the gas to be measured can be provided.

DESCRIPTION OF PREFERRED EMBODIMENTS

Figure 1:
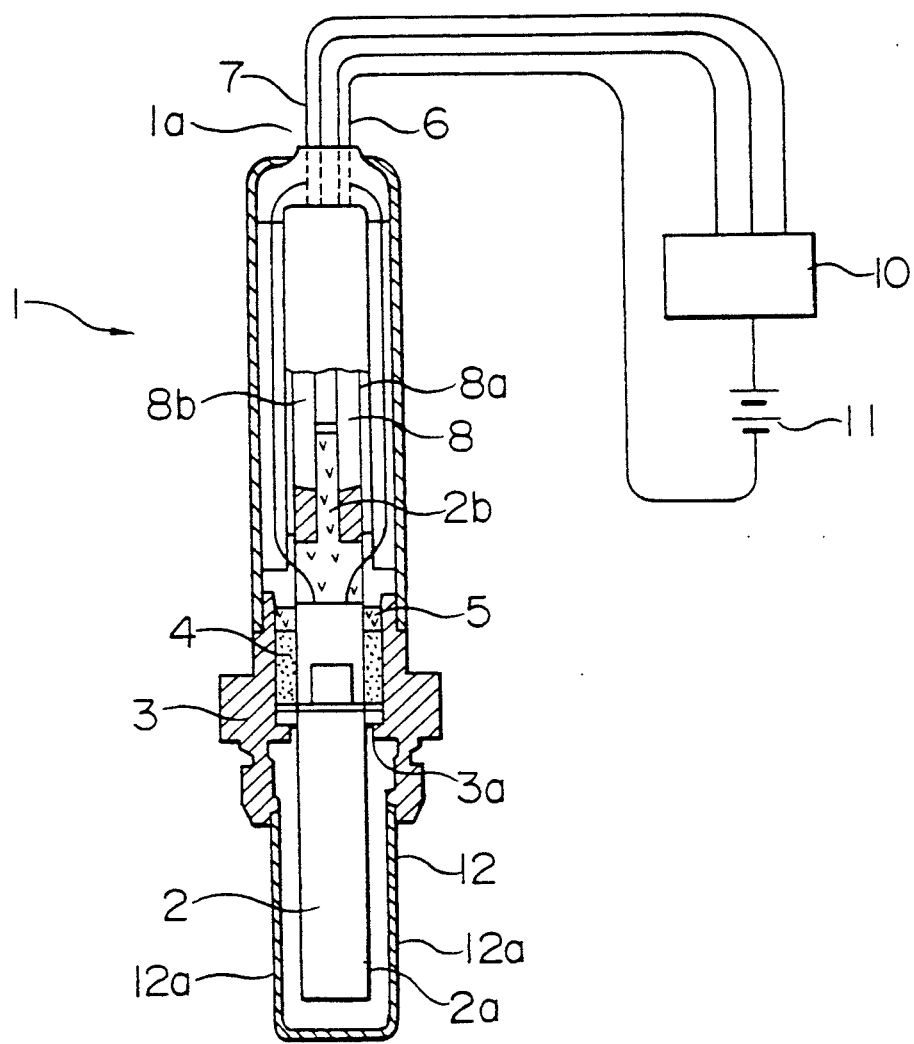
FIG. 1 is a diagram showing the arrangement of an oxygen concentration sensor of a first embodiment according to the present invention.

FIG. 1 is a diagram showing the arrangement of an oxygen concentration sensor 1 mounted in the suction pipe of an internal combustion engine for sensing an EGR ratio with a pinpoint accuracy by sensing an oxygen concentration in a gas to be measured which is a mixed gas composed of intake air and EGR gas.

In FIG. 1, 2 designates a rectangular parallelepiped element composed of a sensor portion 2a exposed to a gas to be measured and a lead-take-out portion 2b. The lead-taking-out portion 2b side is inserted into the cavity portion 3a of a housing 3 and the element 2 is hermetically fixed to the cavity portion 3a of the housing 3 by a heat resistant inorganic adhesive material 4 and further by a heat resistant glass 5 located on the atmospheric side of the inorganic adhesive material 4.

Lead wires 6, 7 each composed of a pair of wires coming from the lead-take-out portion 2b of the element 2 extend to the lead-take-out portion 1a of the oxygen concentration sensor 1 through connection pins 8a, 8b fixed to a cylindrical connector 8. These lead wires 6 and 7 are connected to an imposed voltage control unit 10 used as an imposed voltage control means and a battery 11 at the lead-taking-out portion 1a.

Figure 2:
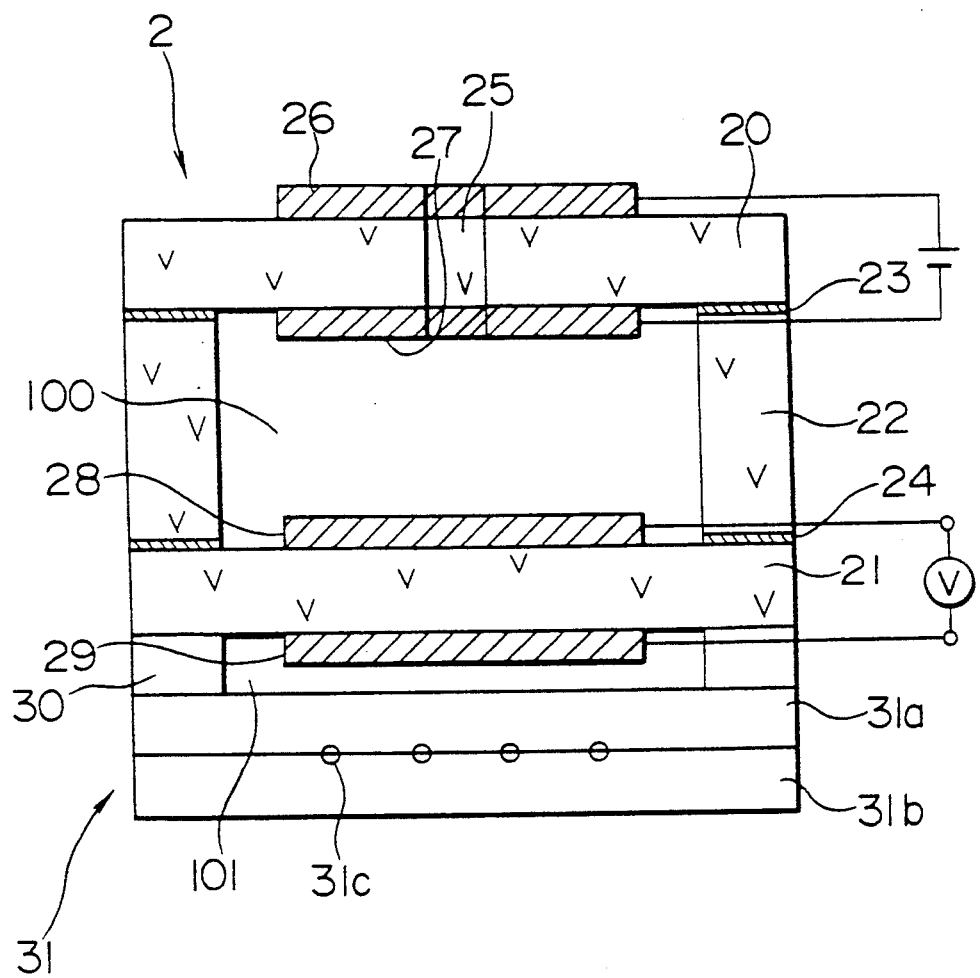
FIG. 2 is a cross sectional view showing an element of the oxygen concentration sensor of the first embodiment according to the present invention.

A protection cover 12 is formed around the sensor portion 2a, which is directly exposed to the gas to be measured, of the element 2 for protecting the element 2 from the gas, the protection cover 12 being fixed to the housing 3 by welding and having an infinite number of communication holes 12a defined therethrough for enabling the element 2 to come into direct contact with the gas to be measured FIG. 2 shows a cross sectional view of the arrangement of the sensor portion 2a of the element 2 shown in FIG. 1.

The element 2 is composed of a chamber portion 100 having a volume of 1 mm$^3$ surrounded by oxygen ion conductive solid electrolytes 20, 21 and 22 mainly composed, for example, of zirconia ($ZnO_2$) and yttria ($Y_2O_3$).

The solid electrolyte 20 has a diffusion hole 25 having a diameter of about 0.7 mm and length of 0.25 mm defined therethrough and confronting pump electrodes 26, 27 each composed of a platinum paste are formed on the opposite surfaces thereof in such a manner that the pump electrode 26 is exposed to the gas to be measured side and the pump electrode 27 is exposed to the chamber portion 100 side.

The solid electrolyte 21 has confronting sensor electrodes 28, 29 formed on the opposite surfaces thereof, the sensor electrode 28 being exposed to the inside of the chamber portion 100. Further, a heating element 31 is formed to the sensor electrode 29 side through a spacer 30. A reference chamber 101 communicating to the gas to be measured is formed at the side of the sensor electrode 29 by the solid electrolyte 21, spacer 30 and heating element 31.

Insulation sheets 23 and 24 are interposed between the solid electrolytes 20 and 22 and between the solid electrolytes 21 and 22, respectively, to thereby prevent an electric affect caused between the concentration electromotive forces of the sensor electrodes 28, 29 produced by a voltage imposed on the pump electrodes 26, 27.

The heating element 31 is composed of a waveshaped platinum heating wire 31c held between sheets 31a and 31b composed of alumina or the like, and the heating element 31 generates heat by imposing a voltage to the heating wire 31c to thereby keep the solid electrolytes 20, 21 and 22 at a predetermined temperature.

The oxygen concentration sensor 1 is connected to the battery 11 through the lead wire 6 and imposed voltage control unit 10 so that a voltage can be imposed between the pump electrodes 26, 27. In addition, the imposed voltage control unit 10 is electrically connected between the sensor electrodes 28, 29 through the lead wire 7 so that an oxygen concentration electromotive force produced by an oxygen partial pressure difference between a pressure inside the chamber portion 100 and the gas to be measured can be input to the imposed voltage control unit 10.

Figure 3:
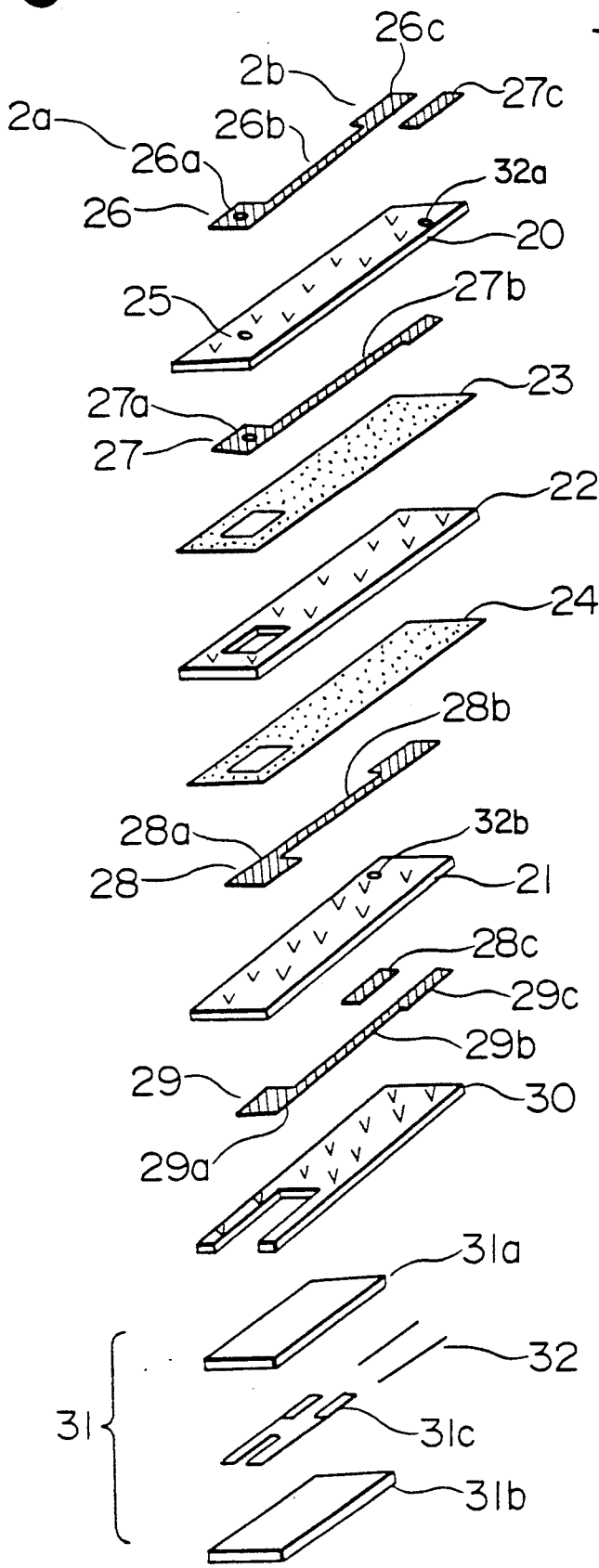
FIG. 3 is an exploded perspective view of the oxygen concentration sensor of the first embodiment according to the present invention.

FIG. 3 shows an exploded perspective view of the element 2 of a first embodiment. A method of manufacturing the element 2 will be described in detail with reference to FIG. 3.

First, the pump electrodes 26, 27 and sensor electrodes 28, 29 are formed in such a manner that confronting platinum electrodes are printed to predetermined shapes on the opposite surfaces of prior-to-bake oxygen ion conductive solid electrolytes 20 and 21 which are prior-to-bake green sheets mainly composed of zirconia and yttria. As shown in FIG. 3, the respective electrodes have such shapes that they are formed to sensing portions 26a, 27a, 28a and 29a each having an area corresponding to substantially a surface of the chamber portion 100 at the portions corresponding to the sensor portion 2a of the element 2, formed to lead shapes serving as lead portions 26b, 27b, 28b and 29b for respective electrodes between the sensor portion 2a and the lead-taking-out portion 2b, and further formed as electrodes each having a predetermined area to be easily taken out as taking-out portions 26c, 27, 28c and 28c at the portion corresponding to the lead-taking-out portion 2b of the element 2.

Through-holes 33a and 33b are formed at the portions corresponding to the lead-taking-out portion 2b of the element 2 of the prior-to-bake solid electrolytes 20 and 21, these through-holes 32a and 33b being defined at such positions that they do not overlap each other, and thus the pump electrode 27 of the prior-to-bake solid electrolyte 20 is led to the same surface as that of the pump electrode 26 and the taking-out portion 27c of the pump electrode 27 is led to the same surface as that of the taking-out portion 26c, respectively, via the through hole 32a. Similarly, the sensor electrode 28 of the prior-to-bake solid electrolyte 21 is led to the same surface as that of the sensor electrode 29 and the taking-out portion 28c of the sensor electrode 28 is positioned on the same surface as that of the taking-out portion 29c of the sensor electrode 29 via the through hole 33b.

Insulation layers 23 composed of alumina (Al$_2$O$_3$) are printed on the opposite surfaces of the prior-to-bake solid electrolyte 22 which is a green sheet mainly composed of zirconia (ZnO$_2$) and yttria (y$_2$O$_3$).

A spacer 30 composed of a green sheet mainly composed of zirconia (ZnO$_2$) and yttria (Y$_2$O$_3$) is laid on the sensor electrode 29 side of the prior-to-bake solid electrolyte 21, the lateral side of the spacer 30 corresponding to the side of the sensor portion 2a of the element 2 being formed to a C-shape is shown in FIG. 3.

Then, the prior-to-bake solid electrolyte 20 having the pump electrodes 26, 27 formed on the opposite surfaces thereof, the prior-to-bake solid electrolyte 22 having the insulation layers formed on the opposite surfaces thereof and the solid electrolyte having the sensor electrodes 28, 29 formed on the opposite surfaces thereof are sequentially overlapped each other. A square hole is formed to each of the prior-to-bake solid electrolyte 22 and insulation layers 23, 24 at a portion corresponding to the sensor portion 2a of the element 2 for forming the chamber portion 100.

As described above, the sequentially laminated components of the prior-to-bake element 2 are fixed under pressure and then baked to convert the green sheets to the solid electrolytes. The thus obtained chamber portion 100 of the oxygen concentration sensor 1 of the first embodiment 1 has a volume of about 1 mm$^3$.

Further, after the element 2 has been baked, a diffusion hole 25 having a diameter of 0.7 mm and a length of 0.25 mm is formed by a drill or the like.

The heating element 31 is arranged such that the heating wire 31c composed of a conductive paste of, for example, platinum or the like and metal wires 32 composed of platinum and connected to the taking-out portion of the heating wire 31c are held between the green sheets 31a and 31b composed of two insulation materials. This heating wire 31c is formed to the wave-shape at the portion thereof corresponding to the sensor portion 2a and has the predetermined area at the portion thereof corresponding to the lead-taking-out portion 2b so that it can be easily taken out.

Thereafter, this laminated member is baked to obtain the heating element 31.

This heating element 31 is adhered to the spacer 30 of the element 2 on the surface thereof confronting the baked solid electrolyte 21 by an inorganic adhesive material.

Next, the operation of the oxygen concentration sensor 1 will be described with reference to FIGS. 2, 5 and 6.

First, when a voltage is imposed between the pump electrodes 26, 27 of the oxygen concentration sensor 1 by the imposed voltage control unit 10 and battery 11, a current flows therethrough so that oxygen ions in the chamber portion 100 are transmitted to the side of gas to be measured outwardly of the chamber portion 100.

As the oxygen ions are transmitted, the gas to be measured flows into chamber portion 100 through the diffusion hole 25 having the predetermined area only in an amount corresponding to the amount of the oxygen ions transmitted by the pump current. Consequently, an oxygen partial pressure in the chamber portion 100 is reduced to thereby produce an oxygen concentration electromotive power between the sensor electrodes 28 and 28 which is produced by an oxygen partial pressure difference between the pressure inside the chamber portion 100 and the pressure outside the chamber portion 100.

Figure 4:
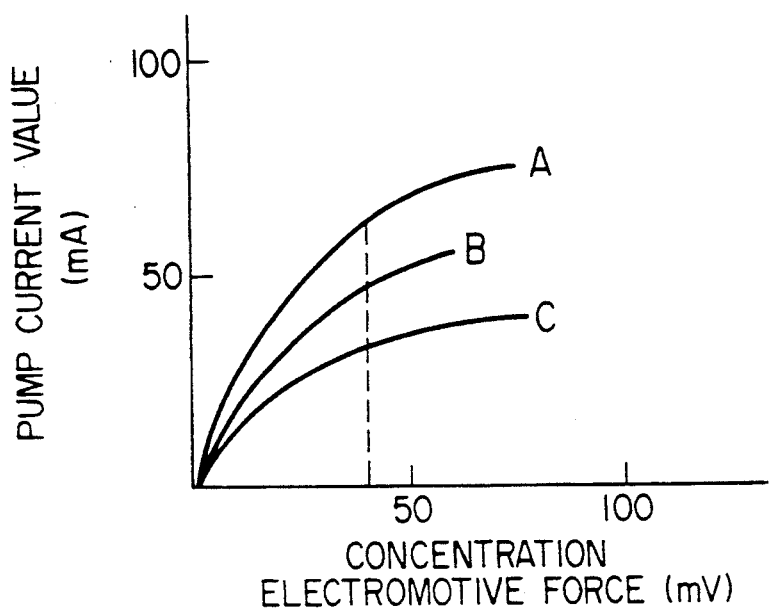
FIG. 4 is a graph showing the relationship between a concentration electromotive force and imposed voltage value at respective oxygen concentrations of the oxygen concentration sensor of the first embodiment.

FIG. 4 is a graph showing the relationship between a sensor electromotive force which is a concentration electromotive force produced between the sensor electrodes 28, 29 and a pump current value resulting from a voltage value imposed between the pump electrodes 26, 27 at oxygen concentrations of 10% (A in FIG. 4), 15% (B in FIG. 4) and 20% (C in FIG. 4).

As apparent from FIG. 4, it is found that a pump current value to a concentration electromotive force is changed as an oxygen concentration of the gas to be measured is changed. In particular, it is found that as an oxygen concentration of the gas to be measured is changed to 10%, 15% and 20%, a pump current is also changed to 30 mA, 50 mA and 70 mA in proportion to the oxygen concentrations, and thus a voltage corresponding to these current values must be imposed in order to maintain a concentration electromotive force at a constant value of, for example, 40 mV.

It is found from the above-mentioned matters that, when a voltage imposed between the pump electrodes 26, 27 is controlled so that a concentration electromotive force produced between the sensor electrodes 28, 29 has a constant value, a pump current value resulting from the imposed voltage is proportional to an oxygen partial pressure difference caused by an oxygen concentration, and thus an oxygen concentration of the gas to be measured can be sensed by using the pump current value as a sensor output.

Figure 5:
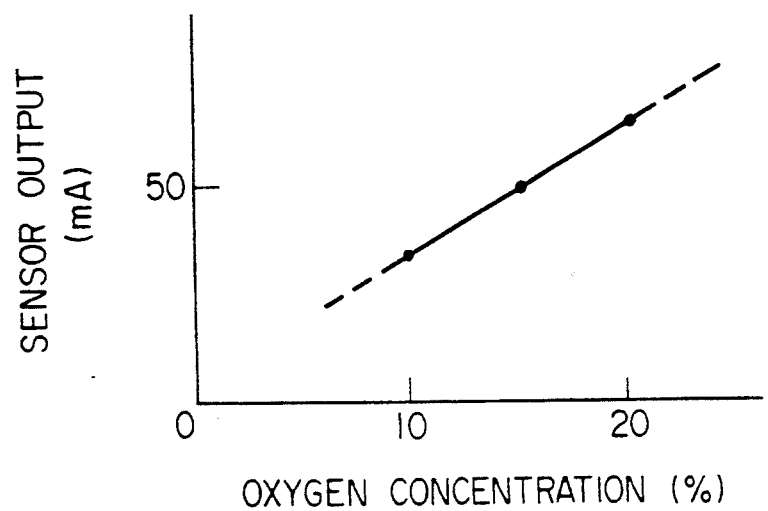
FIG. 5 is a graph showing the relationship between an oxygen concentration and an imposed voltage value when a concentration electromotive force of the oxygen concentration sensor of the first embodiment is kept constant.

FIG. 5 shows the relationship between an oxygen concentration and a sensor output which is a pump current value when a voltage value imposed between the pump electrodes 26, 27 is controlled to maintain an oxygen electromotive force at the constant value of 40 mV, and as apparent from FIG. 5, a sensor output proportional to an oxygen concentration can be obtained by maintain an oxygen electromotive force at a constant value.

Next, the optimization of the size of the diffusion hole 25 and chamber portion 100 which is a characteristic portion of the present invention will be described in detail with reference to FIGS. 6 and 7.

First, as a result of the examination of the reason why an output signal is changed when a pressure of a gas to be measured changes abruptly, the inventors have found that, since a pressure in the chamber 100 is abruptly changed through the diffusion hole 25 by the abrupt change of the pressure of the gas to be measured, an oxygen partial pressure difference between the pressure inside the chamber portion 100 and the gas to be measured is abruptly changed and thus an oxygen concentration partial pressure is also abruptly changed.

Thus, the inventors have paid attention to and studied a length l (mm) and cross sectional area (mm$^2$) of the diffusion hole and a volume (mm$^3$) of the chamber portion 100 to obtain an oxygen concentration sensor which is not affected by a pressure variation in the chamber 100 even if the pressure of a gas to be measured is abruptly changed.

Figure 6:
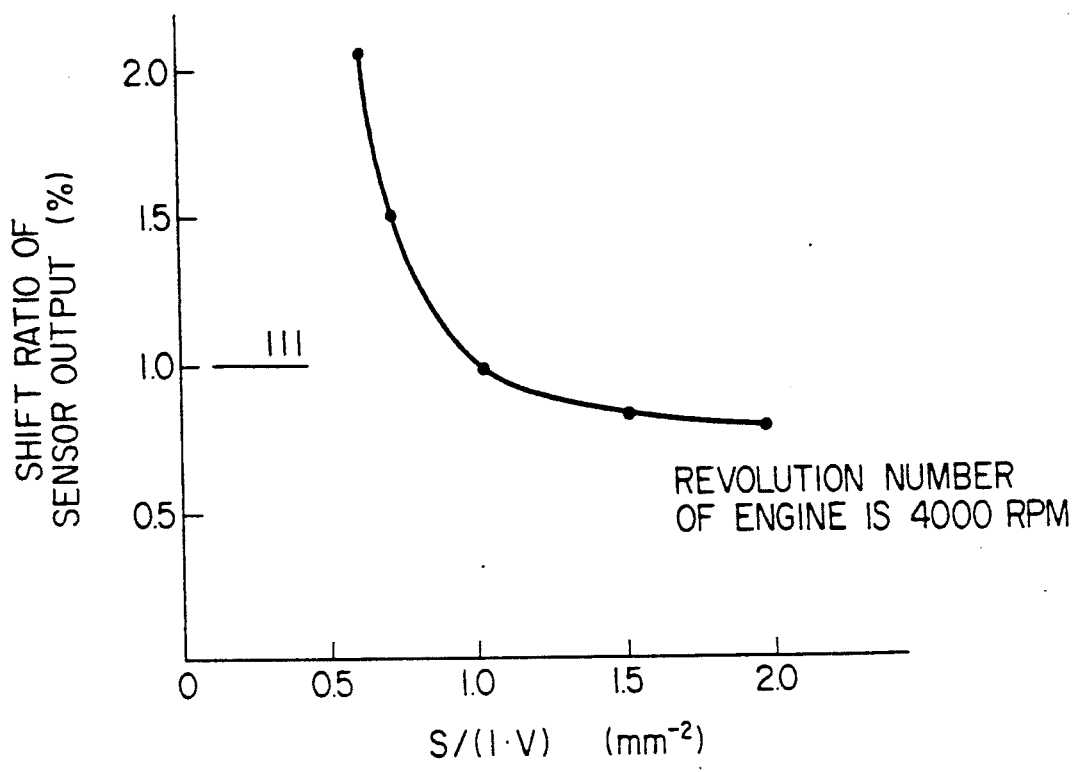
FIG. 6 is a graph showing the relationship between an intrinsic characteristic value and a degree of shift of a sensor output.

FIG. 6 shows the relationship between a value obtained from S/(l·V) (mm$^{-2}$) (hereinafter, referred to as an intrinsic characteristic value), where l (mm) and S (mm$^2$) represent a length and cross sectional area of the diffusion hole, respectively and V (mm$^3$) represents a volume of the chamber 100, and a degree of shift from a normal state of an imposed electromotive force in an abrupt pressure variation (for example, a pressure variation with a pressure difference of 20 mHg arising 100 times per minute when an engine is rotated at 3200 r.p.m). The degree of shift used here shows a degree of shift of a sensor output from the state at which an engine is stationary to the state at which the engine is in operation.

As apparent from FIG. 6, it can be easily understood that an oxygen concentration sensor with a conventional intrinsic characteristic value of 1.0 mm$^{-2}$ or less has a very large degree of shift of a pump current value and thus is greatly affected by a dynamic pressure variation as the abrupt pressure variation of a gas to be measured.

Figure 7:
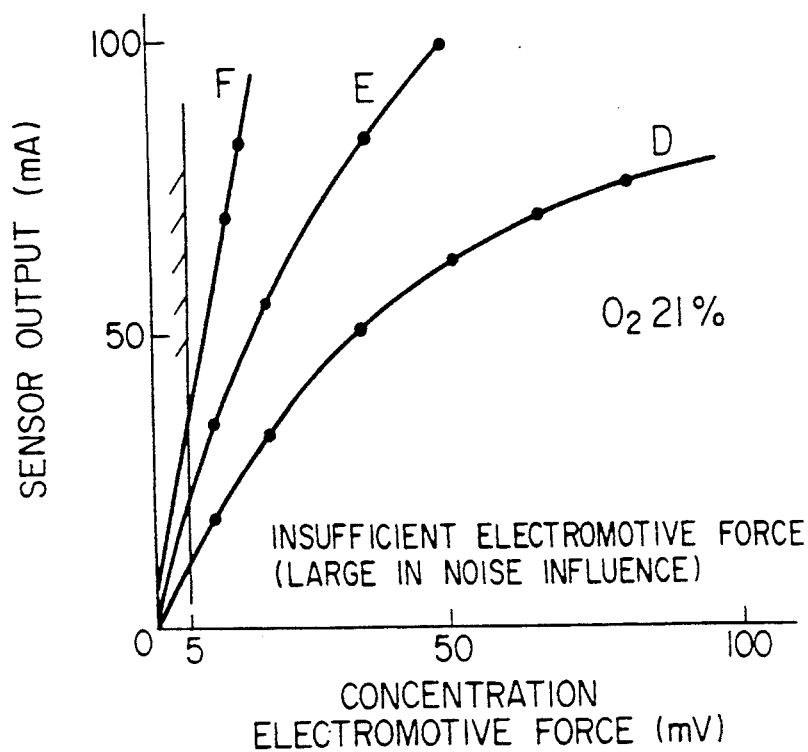
FIG. 7 is a graph showing the relationship between an oxygen concentration electromotive force and an imposed voltage value at respective intrinsic characteristic values.

FIG. 7 shows the relationship between a concentration electromotive force produced between the sensor electrodes 28 and 29 and a sensor output at respective intrinsic values 1.5 mm$^{-2}$ (D in FIG. 7), 5 mm$^{-2}$ (E in FIG. 7) and 6 mm$^{-2}$ (F in FIG. 7) when an oxygen concentration is 21%.

As apparent from FIG. 7, it can be easily understood that when an intrinsic characteristic value is larger than 5 mm$^{-2}$, a concentration electromotive force is made very small and thus an oxygen concentration cannot be correctly sensed.

From the above-mentioned, the inventors have found for the first time that when a value of S/(l·V) (mm$^{-2}$) representing the intrinsic characteristics value is in the range from 1 mm$^{-2}$ to 5 mm$^{-2}$, an oxygen concentration can be correctly sensed without being affected by the dynamic pressure variation of a gas to be measured.

Figure 8:
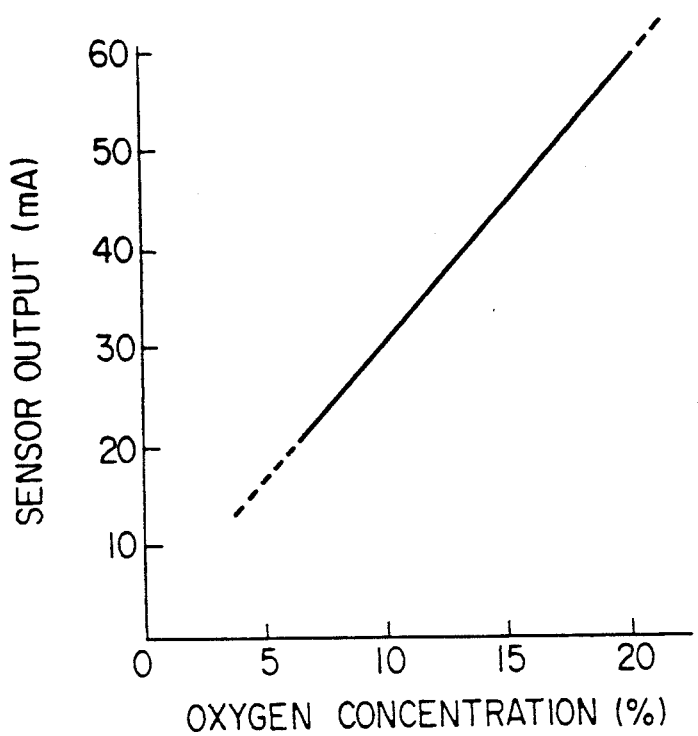
FIG. 8 is a characteristic diagram showing the characteristics of the oxygen concentration sensor of the first embodiment according to the present invention.
Figure 9:
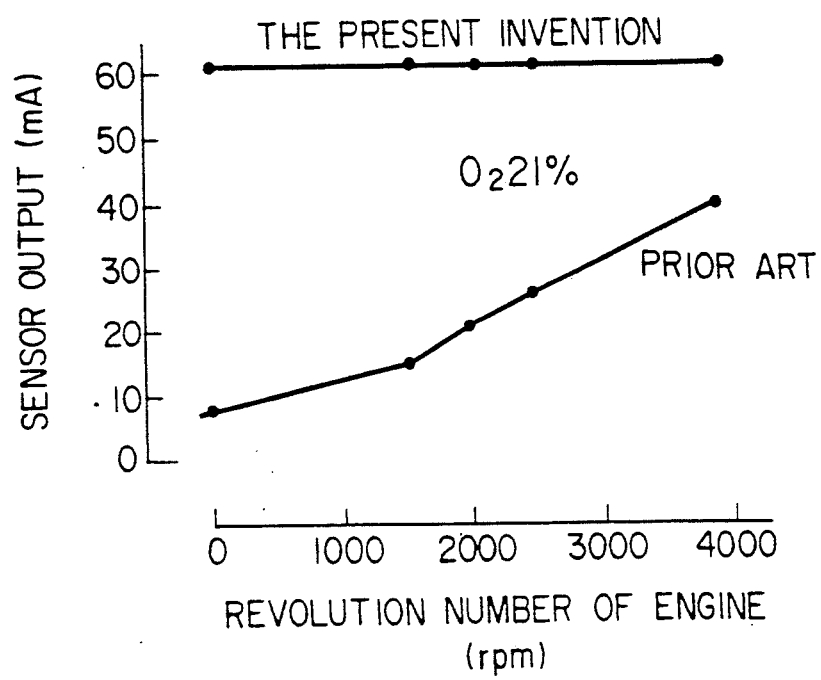
FIG. 9 is a characteristic diagram showing the characteristics of the oxygen concentration sensor of the first embodiment according to the present invention and the characteristics of a conventional oxygen concentration sensor.

Next, FIGS. 8 and 9 shows the characteristics of the oxygen concentration sensor 1 of the first embodiment having an intrinsic characteristic value of 1.54 which is within the range from 1 to 5.

FIG. 8 shows the relationship between a change of an oxygen concentration and a sensor output. As apparent from FIG. 8, even if the oxygen concentration sensor 1 according to the present invention has an intrinsic characteristic value larger than that of a conventional oxygen concentration sensor, a sensor output resulting from an imposed voltage value is proportional to an oxygen concentration similarly to the conventional oxygen concentration sensor, and thus the oxygen concentration sensor 1 can correctly senses an oxygen concentration in the occurrence of a static pressure variation and the like.

Further, since a volume of the chamber portion 100 and a length of the diffusion hole 25 of the oxygen concentration sensor 1 of the first embodiment are smaller than those of the conventional oxygen concentration sensor and a cross sectional area of the diffusion hole 25 of the former is larger than that of the latter, the gas to be measured can easily flow to the chamber portion, and thus a sensor output can be increased and further a responsiveness can be shortened to 100 msec. as compared with a conventional responsiveness of, for example, 800 msec.

FIG. 9 shows the relationship between an engine r.p.m and a sensor output in the oxygen concentration sensor 1 of the first embodiment and a conventional oxygen concentration sensor having an intrinsic characteristic value of $7.5 \times 10^3$.

As apparent from FIG. 9, the conventional oxygen concentration sensor is directly affected by the dynamic pressure variation of a mixed gas composed of an intake air and EGR caused by the change of an engine r.p.m and a sensor output is changed accordingly, and thus an oxygen concentration cannot be correctly sensed. The oxygen concentration sensor 1 of the first embodiment, however, can provide an excellent advantage that, even if the oxygen concentration sensor 1 is subjected to the dynamic pressure variation of a mixed gas, a sensor output is not almost changed by specifying a length and cross sectional area of the diffusion hole and a volume of the chamber portion by the given relational expression.

Figure 10:
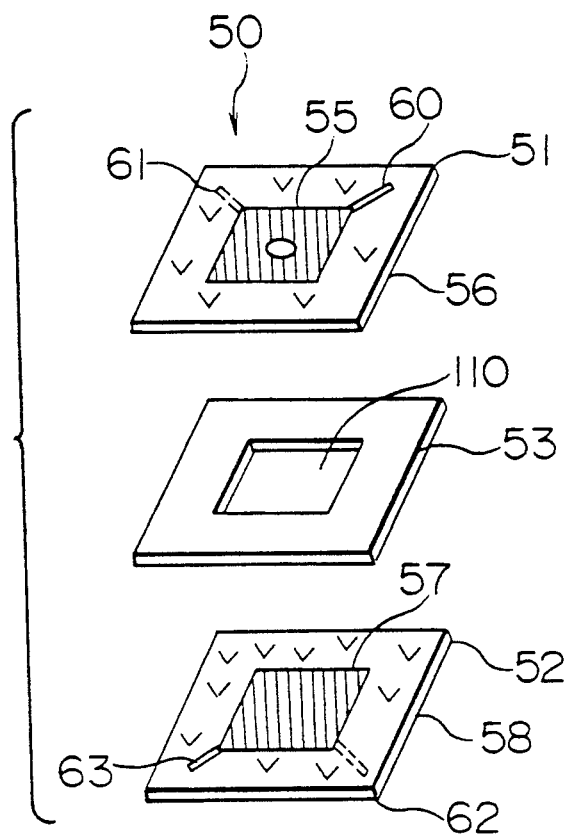
FIG. 10 is a diagram showing the arrangement of a second embodiment according to the present invention.
Figure 14:
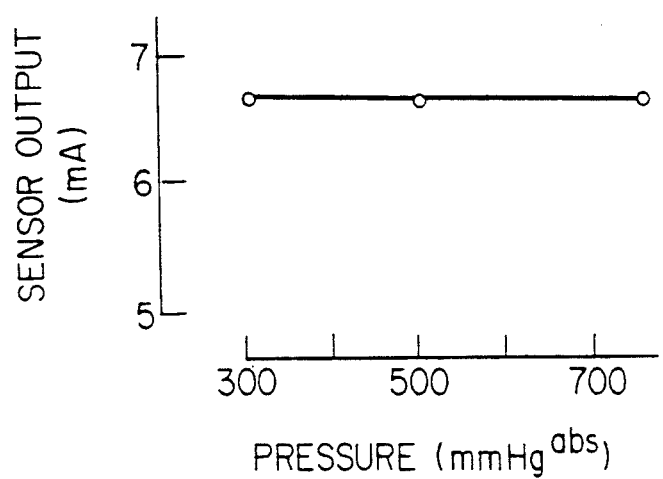
FIG. 14 is a characteristic diagram showing the characteristics of a conventional oxygen concentration sensor.

Next, a second embodiment of the present invention will be described with reference to FIG. 10.

Although the aforesaid element has a rectangular parallelepiped shape, the second embodiment has a chip shape.

An oxygen concentration sensor 50 has a chamber 110 with a volume of 1 mm$^3$ surrounded by a pair of confronting solid electrolytes 51, 52 and spacer 53, the chamber 110 being formed by interposing a spacer 53 defined with a square hole between the solid electrolytes 51, 52.

A diffusion hole 54 having a diameter of 0.7 mm and a length of 0.25 mm is defined through the solid electrolyte 51 and pump electrodes 55, 56 are also formed on the opposite surfaces of the solid electrolyte 51.

Further, sensor electrodes 57, 58 are formed on the opposite surfaces of the solid electrolyte 52.

Lead wires 60, 61, 62 and 63 are electrically connected to the respective electrodes 55, 56, 57 and 58.

The oxygen concentration sensor of the second embodiment has the same operation and advantage as those of the above first embodiment.

Figure 11:
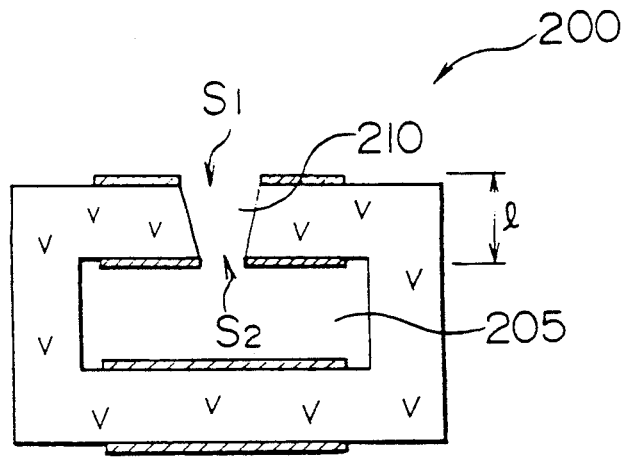
FIG. 11 is a diagram showing the arrangement of a third embodiment according to the present invention.

FIG. 11 shows an oxygen concentration sensor 200 of a third embodiment.

The oxygen concentration sensor 200 of the third embodiment has a diffusion hole 210 having a cross sectional area which is continuously made smaller toward a chamber portion 205.

A cross sectional area S and length L of the diffusion hole of the present invention in the case of the diffusion hole 210 with a changing radius can be expressed as follows because the value S/L of the present invention is only used to show how easily a gas to be measured enters the chamber portion.

That is, in FIG. 11, S of the present invention is determined as follows, where S1 represents a maximum cross sectional area of the diffusion hole and S2 represents a minimum cross sectional area thereof.

$$S = (S1 + S2)/2$$

When the oxygen concentration sensor 200 of the third embodiment satisfies the following expression, the thus obtained oxygen concentration sensor has the same operation and advantage as those of the aforesaid first embodiment.

$$1 \leq S/(L \cdot V) \leq 5$$

Figure 12:
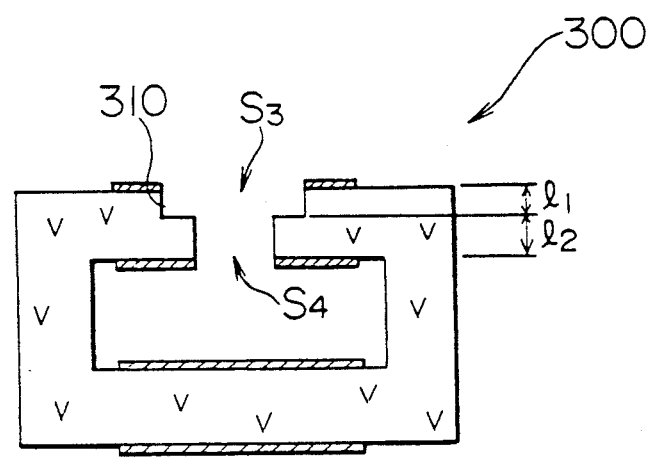
FIG. 12 is a diagram showing the arrangement of a fourth embodiment according to the present invention.

FIG. 12 shows an oxygen concentration sensor 300 of a fourth embodiment.

In the oxygen concentration sensor 300 of the fourth embodiment, S/(L·V) of the present invention can be determined as follows, where a diffusion hole 310 has cross sectional area S3 and S4 and lengths L1 and L2, respectively.

That is, since $S = (S1 \cdot L1 + S2 \cdot L2)/(L1 + L2)$, $$S/(L \cdot V) = (S1 \cdot L1 + S2 \cdot L2)/[(L1 + L2)^2 \cdot V]$$

When the oxygen concentration sensor 400 of the fourth embodiment satisfies the following expression, the thus obtained oxygen concentration sensor has the same operation and advantage as those of the aforesaid first embodiment.

$$1 \leq S/(L \cdot V) \leq 5$$

Figure 13:
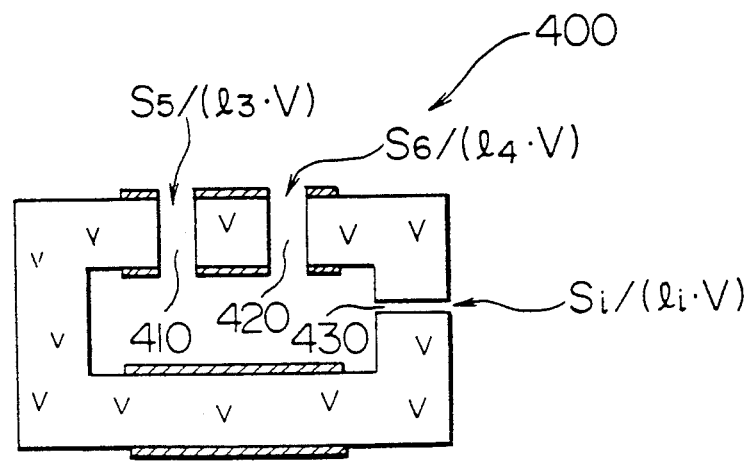
FIG. 13 is a diagram showing the arrangement of a fifth embodiment according to the present invention.
Figure 15:
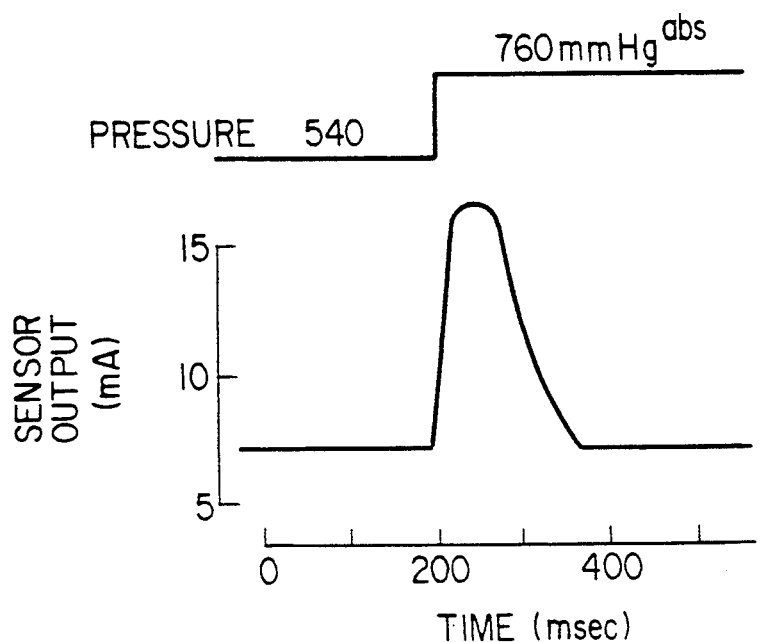
FIG. 15 is a characteristic diagram showing the characteristics of a conventional oxygen concentration sensor.
Figure 16:
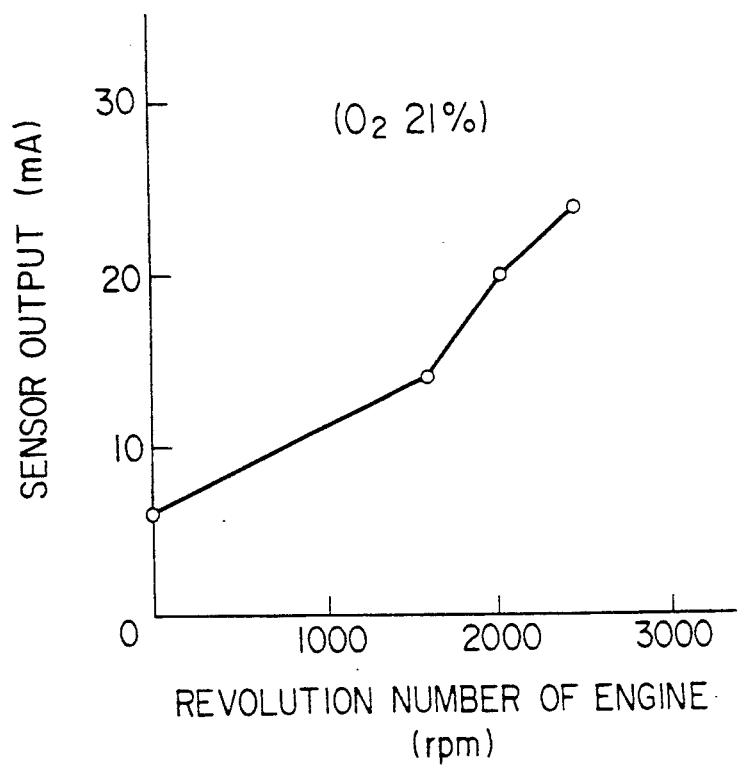
FIG. 16 is a characteristic diagram showing the characteristics of a conventional oxygen concentration sensor.

FIG. 13 shows an oxygen concentration sensor 400 of a fifth embodiment.

The oxygen concentration sensor 400 of the fifth embodiment is defined with a diffusion hole 410 having a length L3 and a cross sectional area S5, a diffusion hole 420 having a length L4 and a cross sectional area S6, ..., and a diffusion hole 430 having a length Li and a cross sectional area Si.

When a plurality of the diffusion holes 410, 420 and 430 are defined as described above, S/(L·V) of the present invention can be determined as follows.

That is, S/(L·V) of the present invention is equal to the total of Si/(Li·Vi) (where, i is an integer).

When the oxygen concentration sensor 400 of the fifth embodiment satisfies the following expression, the thus obtained oxygen concentration sensor has the same operation and advantage as those of the aforesaid first embodiment.

$$1 \leq S/(L \cdot V) \leq 5$$

The present invention is not limited to the above embodiments and may have the following arrangements.

More specifically, in the above first embodiment, although the pump electrodes are formed to the solid electrolyte through which the diffusion hole is defined and the sensor electrodes are formed to the solid electrolyte confronting the above solid electrolyte, the positional relationship between the pump electrodes and the sensor electrodes is not limited to the above, and, for example, the sensor electrodes may be formed on the side of the solid electrolyte through which the diffusion hole is defined.

In the above first embodiment, although the diffusion hole is defined through the solid electrolyte, the present invention is not limited thereto and it may be formed to anywhere so long as the chamber portion is communicated with a gas to be measured therethrough.

In the above embodiments, although the heating element is formed to the sensor electrode side, the position where the heating element is mounted is not limited thereto, and it may be formed, for example, to the pump electrode side.

Further, in the above embodiments, although the heating member and the element are individually baked, the heating member may be formed on the solid electrolyte by a screen printing or the like and the heating member is baked integrally with the element.

Further, the pump electrodes and sensor electrodes may be formed on the opposite sides of the same solid electrolyte. In this case, since the pump electrodes and sensor electrodes are formed on the same solid electrolyte, a concentration electromotive force produced to the sensor electrodes is liable to be affected by a voltage imposed on the pump electrodes, and thus an insulation sheet or the like may be interposed between both the electrodes.

Furthermore, confronting electrodes serving as both the pump and sensor electrodes may be formed on the opposite surfaces of the solid electrolyte, wherein these electrodes are used as the pump electrodes by imposing a voltage thereon for a predetermined time, and thereafter used as the sensor electrodes for sensing a concentration electromotive force produced between the chamber portion and a gas to be measured by interrupting the application of the voltage. An oxygen concentration of a gas to be measured may be sensed when necessary by forming confronting electrodes only at a location which alternately perform the above operations.

As described above, according to the present invention, there is provided an oxygen concentration sensor having a specified size of a diffusion hole and a specified volume of a chamber portion, by which an oxygen concentration can be correctly measured even if a dynamic pressure outside the chamber portion is abruptly changed and a fuel consumption of an internal combustion engine can be improved.

What is claimed is:

1. An oxygen concentration sensor, comprising:

an element, adapted to be exposed to a gas to be measured and having a chamber portion formed together with an oxygen ion conductive solid electrolyte having confronting electrodes formed on the opposite surfaces thereof, for measuring an oxygen concentration of said gas to be measured at least during a time when pressure of said gas to be measured varies; and means for defining a restricted diffusion hole for restricting the flow of said gas to be measured into said chamber portion, wherein said restricted diffusion hole has the relationship $1 \leq S/(L \cdot V) \leq 5$ with respect to said restricted diffusion hole and said restricted diffusion hole having a cross sectional area S ($mm^2$) and a length L (mm) and said chamber portion having a volume V ($mm^3$).

2. An oxygen concentration sensor according to claim 1, wherein said electrodes formed on said solid electrolyte comprise pump means for transmitting oxygen ions in said chamber portion in a direction toward said gas to be measured when a voltage is applied thereto, and sensor means for sensing a concentration electromotive force produced by an oxygen partial pressure difference between a pressure inside said chamber portion and said pressure of said gas to be measured.

3. An oxygen concentration sensor, comprising:

an element, adapted to be exposed to a gas to be measured and having a box-shaped chamber having at least one surface comprising an oxygen ion conductive solid electrolyte;

means for defining a restricted diffusion hole for communicating said chamber of said element with said gas to be measured and restricting the flow of said gas to be measured into said chamber;

pump electrodes, formed on confronting opposite surfaces of said solid electrolyte, for transmitting oxygen ions in said chamber in a direction toward said gas to be measured when a voltage is applied thereto;

sensor electrodes, formed on confronting opposite surfaces of said solid electrolyte, for sensing, at least during a time when pressure of said gas to be measured varies, an oxygen concentration difference between the inside of said chamber and said gas to be measured and providing an oxygen concentration electromotive force representative thereof; and voltage control means for controlling a voltage value applied to said pump electrodes to maintain said oxygen concentration electromotive force, provided by said sensor electrodes, substantially constant;

wherein the restricted diffusion hole has a relationship of $1 \leq S/(L \cdot V) \leq 5$ with respect to said restricted diffusion hole and said restricted diffusion hole having a cross sectional area S ($mm^2$) and a length L (mm) and said chamber portion having a volume V ($mm^3$).

* * * * *